United States Patent
Voigt et al.

(10) Patent No.: US 10,386,010 B2
(45) Date of Patent: Aug. 20, 2019

(54) STAND AND METHOD FOR TORQUE COMPENSATION

(71) Applicant: Carl Zeiss Meditec AG, Jena (DE)

(72) Inventors: Christian Voigt, Abtsgmuend (DE); Christine Hanel, Oberkochen (DE); Dominik Litsch, Schorndorf (DE)

(73) Assignee: Carl Zeiss Meditec AG, Jena (DE)

( * ) Notice: Subject to any disclaimer, the term of this patent is extended or adjusted under 35 U.S.C. 154(b) by 98 days.

(21) Appl. No.: 15/404,111

(22) Filed: Jan. 11, 2017

(65) Prior Publication Data
US 2017/0198856 A1  Jul. 13, 2017

(30) Foreign Application Priority Data
Jan. 11, 2016 (DE) .......... 10 2016 200 214

(51) Int. Cl.
| | |
|---|---|
| *G02B 7/00* | (2006.01) |
| *F16M 11/18* | (2006.01) |
| *A61B 90/25* | (2016.01) |
| *F16M 11/10* | (2006.01) |
| *F16M 11/20* | (2006.01) |
| *F16M 11/42* | (2006.01) |

(52) U.S. Cl.
CPC ............ *F16M 11/18* (2013.01); *A61B 90/25* (2016.02); *F16M 11/10* (2013.01); *F16M 11/2014* (2013.01); *F16M 11/2021* (2013.01); *F16M 11/42* (2013.01); *F16M 2200/044* (2013.01); *F16M 2200/063* (2013.01)

(58) Field of Classification Search
CPC ........ B25J 9/1633; A61B 90/25; A61B 90/20; A61B 90/35; A61B 90/50; A61B 2090/508; A61B 1/045; F16M 11/2092; F16M 11/10; F16M 11/38; F16M 13/02; F16M 11/42; G02B 21/0012; G02B 21/24; G02B 7/00; G02B 21/362; G02B 21/365
USPC ................... 700/245; 248/157, 124.1, 276.1; 359/365, 384, 390
See application file for complete search history.

(56) References Cited

U.S. PATENT DOCUMENTS

| | | | | |
|---|---|---|---|---|
| 4,515,333 A | * | 5/1985 | Pugh ................ | F16C 11/106 248/123.11 |
| 4,741,607 A | * | 5/1988 | Heller ............... | F16M 11/08 248/123.2 |

(Continued)

FOREIGN PATENT DOCUMENTS

DE  10 2004 008 381 A1  1/2005

*Primary Examiner* — Dalena Tran
(74) *Attorney, Agent, or Firm* — Walter Ottesen, P.A.

(57) ABSTRACT

A stand, for example, for mounting a medical instrument, has a first part and second part which is connected to the first part in a rotationally movable manner via a rotary joint and can be moved relative to the first part about an axis of rotation. The stand includes a drive module supported on the first part. The module has a drive member coupled to the second part. A control device having a controller is connected to the drive module and intended for setting a drive torque provided by the drive member. The control device includes a torque sensor for detecting a torque acting on the second part and a control-signal assembly connected to the controller. The control-signal assembly from the torque detected and a setpoint value generates a signal, which is fed to the controller and is intended for setting the drive torque provided by the drive member.

19 Claims, 6 Drawing Sheets

(56) References Cited

U.S. PATENT DOCUMENTS

| | | | |
|---|---|---|---|
| 4,943,296 A * | 7/1990 | Funakubo | A61F 9/013 606/166 |
| 5,332,181 A | 7/1994 | Schweizer et al. | |
| 6,216,056 B1 | 4/2001 | Ito et al. | |
| 6,471,165 B2 | 10/2002 | Twisselmann | |

* cited by examiner

STAND AND METHOD FOR TORQUE COMPENSATION

CROSS REFERENCE TO RELATED APPLICATION

This application claims priority of German patent application no. 10 2016 200 214.7, filed Jan. 11, 2016, the entire content of which is incorporated herein by reference.

FIELD OF THE INVENTION

The invention relates to a stand, in particular for mounting a medical instrument, for example a surgical microscope, comprising a first stand part and a second stand part, which is connected to the first stand part in a rotationally movable manner by means of a rotary joint and can be moved relatively in relation to the first stand part about an axis of rotation, comprising a drive module, which is supported on the first stand part and has a drive member coupled to the second stand part, and comprising a control device, which has a controller assembly, which is connected to the drive module and is intended for setting a drive torque that is provided by the drive member of the drive module. The invention also relates to a method for setting a state of equilibrium in the case of such a stand.

BACKGROUND OF THE INVENTION

Such a stand and such a method are known from DE 10 2004 008 381 B4. To compensate for load torques in a rotary joint of the stand, here there are drive modules in the form of electric motors, which are controlled according to the rotational position of the rotary joints picked up by sensors.

The possibility of a largely force-free displacement of medical instruments with a stand is of interest in particular for surgical operations in which an operator has to carry out precision movements manually. Compensating weights and/or elastic energy stores are also widely used in the case of such stands for setting states of equilibrium.

In addition, stands comprising multiple axes of rotation and servo drives for moving medical-optical equipment are also known (U.S. Pat. No. 5,332,181).

SUMMARY OF THE INVENTION

It is an object of the invention to provide a stand having at least one rotary joint that can also be adjusted by an operator in a largely force-free manner by being moved manually, even when heavy instruments are mounted on the stand.

The object can, for example, be achieved by a stand including a first stand part; a rotary joint; a second stand part connected to the first stand part in a rotationally movable manner via the rotary joint; the second stand part being configured to be movable about an axis of rotation relative to the first stand part; a drive module supported on the first stand part; the drive module having a drive member coupled to the second stand part; a control device having a controller assembly; the controller assembly being connected to the drive module and being configured to set a drive torque provided by the drive member of the drive module; the control device including a torque sensor configured to detect a torque (Mi) acting on the second stand part; the control device further including a control-signal assembly connected to the controller assembly; the control-signal assembly being configured to generate a control signal (Mc) from the torque (Mi) detected by the torque sensor and a setpoint drive torque value (Ms) transmitted to the control signal assembly; the controller assembly being configured to receive the control signal (Mc); and, the control signal (Mc) being configured to set the drive torque provided by the drive member of the drive module.

The object can, for example, also be achieved by a method for moving a medical-optical instrument, for example a surgical microscope, mounted on a stand comprising multiple stand parts jointedly connected to one another in pairs by a rotary joint with an axis of rotation, wherein, in the stand, a rotary joint, which connects a first and a second stand part, is in each case assigned a drive module, which is supported on the first stand part and has a drive member coupled to the second stand part, wherein a torque (MI) acting on the second stand part is picked up and a control signal (MC) for setting the drive torque provided by means of the drive member is generated from the picked-up torque (MI) and a setpoint drive torque value (MS).

The invention is based on the concept that, by setting suitable drive torques via a drive module that is assigned to a rotary joint in a stand, it is possible to compensate exactly for torques occurring about the axis of rotation of the rotary joint, by the drive module providing exactly the drive torque required for torque compensation about the axis of rotation of the rotary joint.

A rotary joint is understood in this case as meaning a joint in a stand that connects a first stand part to a second stand part and allows a rotational movement of the first stand part relatively in relation to the second stand part about an axis of rotation and by a certain rotating angle $\varphi$. This rotating angle $\varphi$ may be different from the value $\varphi=360°$. The axis of rotation of the rotary joint in a stand according to the invention may be in particular a pivoting axis or a tilting axis, about which the first stand part can be pivoted or tilted relatively in relation to the second stand part in the rotary joint.

It is proposed according to the invention that the control device includes in the stand a torque sensor for picking up a torque $M_I$ acting on the second stand part, that is, a torque that is introduced into the second stand part, and that the control device has a control-signal assembly, which is connected to the controller assembly and generates from the torque $M_I$ picked up by means of the torque sensor and a setpoint drive torque value $M_s$ transmitted to the control-signal assembly a control signal $M_c$, which is fed to the controller assembly and is intended for setting the drive torque provided by the drive member of the drive module. The control signal $M_c$ generated by the control-signal assembly may be a difference signal $M_c = M_s - M_I$ formed from the torque $M_I$ picked up by means of the torque sensor and the setpoint drive torque value $M_s$ fed to the control signal assembly.

The control device preferably includes an assembly for determining the set-point drive torque value from the movement signal which is fed to the assembly for a rotational movement of the second stand part about the axis of rotation and is from the group comprising the angle of rotation $\varphi$ and/or the change in the angle of rotation $\dot{\varphi}$ and/or the acceleration of the angle of rotation $\ddot{\varphi}$. For determining the setpoint drive torque value, the assembly may comprise in particular a computer unit with a computer program stored therein for calculating the setpoint drive torque value $M_s$ from the movement signal. The drive module may be formed for example as an electric motor.

By coupling the output of the drive module and the second stand part by means of a gear mechanism, it is possible to step up or step down the torques provided by the drive module. The gear mechanism may include in particular a gear assembly with a coupling gear mechanism connected to the second stand part. A coupling gear mechanism is understood in this case as meaning a gear mechanism that converts a rotational movement of a gear element that is rotatably coupled to the drive module, by means of a couple in the form for example of a drive rod or a connecting rod, into a linear movement or an oscillating movement transmitted to the second stand part.

By the gear mechanism comprising a step-down gear mechanism, which is connected to the output and is formed for example as a harmonic-drive gear mechanism, it can be achieved that only small torques have to be generated by the drive module even for moving heavy assemblies.

The inventors have found that not least the gear friction in step-up and step-down gear mechanisms is a reason why torques that are provided by a drive module to compensate for a torque acting on a stand part about an axis of rotation of a rotary joint do not allow exact torque compensation without the gear friction being determined load-dependently or a torque that is introduced into a stand part and is intended to be compensated being measured.

By generating a control signal $M_c$ that is fed to the controller assembly and is intended for setting the drive torque provided by the drive member of the drive module from the torque $M_I$ that is picked up by means of the torque sensor and introduced into the second stand part, in particular by way of the drive member, and a setpoint drive torque value $M_s$ that is transmitted to the control-signal assembly, the force-free moving of the second stand part relatively in relation to the first stand part can be achieved in gear-friction compensation without an additional control device, such as for example a joystick. This measure also allows compensating and/or loading weights on the first stand part and/or the second stand part to be changed without having an effect on the force-free adjustability of the first stand part relatively in relation to the second stand part as a result of the appropriate drive torque that is provided by the drive member of the drive module. In particular, it is not required that control curves for the drive module have to be determined, as is described in DE 10 2004 008 381 B4, for providing the appropriate drive torque for torque compensation for force-free moving of the first stand part relatively in relation to the second stand part.

In order to determine the torque that is introduced into the second stand part, the torque sensor preferably determines the torque that is introduced into the output of the gear mechanism connected to the second stand part.

A stand according to the invention may also have a stand braking mechanism for optionally enabling and disabling a movement of the first stand part relatively in relation to the second stand part about the axis of rotation of the rotary joint. By the stand having a counterweight and/or an elastically deformable energy store for at least partially compensating for a load torque about the axis of rotation that is introduced into the second stand part, it is possible to use drive modules of a low power output, which only generate small drive torques, in the stand.

A stand according to the invention may also include multiple rotary joints, connecting a first stand part to a second stand part, with a drive module which is assigned to the respective rotary joint, is supported on the first stand part and has an output coupled to the second stand part. In the stand there are then a control device, in which there is for each drive module assigned to a rotary joint a control loop with a torque sensor for picking up a torque $M_I^{(n)}$, $M_I^{(n-1)}$, ..., $M_I^{(1)}$ that is introduced into the second stand part, and a control-signal assembly, which is connected to the controller assembly and generates from the torque $M_I^{(n)}$, $M_I^{(n-1)}$, ..., $M_I^{(1)}$ picked up by means of the torque sensor and a setpoint drive torque value $M_s^{(n)}$, $M_I^{(n-1)}$, ..., $M_s^{(1)}$ transmitted to the control-signal assembly a control-signal $M_c^{(n)}$, $M_c^{(n-1)}$, ..., $M_c^{(1)}$, which is fed to the controller assembly and is intended for setting the drive torque provided by the drive member of the drive module. The control device then includes here for each drive module assigned to a rotary joint an assembly for determining the set-point drive torque value which, for determining the setpoint drive torque value $M_s^{(n)}$, $M_I^{(n-1)}$, ..., $M_s^{(1)}$, takes into account a movement signal which is picked up at least for the rotational movement of a second stand part about the axis of rotation of the rotary joint and is from the group comprising the angle of rotation $\varphi$ and/or the change in the angle of rotation $\dot{\varphi}$ and/or the acceleration of the angle of rotation $\ddot{\varphi}$. By at least one assembly for determining the setpoint drive torque value in a control loop also taking into account here for determining the setpoint drive torque value $M_s^{(n)}$, $M_I^{(n-1)}$, $M_s^{(1)}$ a movement signal picked up for the rotational movement of a further second stand part about the axis of rotation of a further rotary joint or multiple movement signals picked up for the rotational movement of further second stand parts about the axis of rotation of further rotary joints from the group comprising the angle of rotation $\varphi$ and/or the change in the angle of rotation $\dot{\varphi}$ and/or the acceleration of the angle of rotation $\ddot{\varphi}$, it is possible by means of the drive modules assigned to the rotary joints to set a state of equilibrium in which the stand can be moved by an operator in a force-free manner not just for individual axes of rotation of the stand, but rather for the stand as a whole.

In particular, one idea of the invention is that the first stand part is formed as a base on which the second stand part is mounted. The second stand part is then a holding arm. For mounting the medical instrument, in this case a pivotally movable supporting arm is preferably connected to the first stand part. A link is provided, articulated on the supporting arm and forming a parallel linkage age with the supporting arm and a further link, which is connected to the first stand part and is displaceable in a pivotally movable manner about the first axis of rotation, and also the holding arm. A further drive module may be provided here, supported on the base and having an output that is coupled to the displaceable further link, and a further control device, which has a controller assembly which is connected to the further drive module and is intended for setting an output torque provided at the output of the drive module. The control device then includes a torque sensor for picking up a torque $M_I$ acting on the further link and has a control-signal assembly, which is connected to the controller assembly and generates from the torque $M_I$ picked up by means of the torque sensor and a setpoint drive torque value $M_s$ transmitted to the control-signal assembly a control signal $M_c$ which is fed to the controller assembly and is intended for setting the output torque provided by the drive of the drive module.

By the method according to the invention for moving a medical instrument mounted on a stand comprising multiple first and second stand parts jointedly connected to one another in pairs by a rotary joint with an axis of rotation, a torque acting on a second stand part, that is, a torque $M_I$ introduced into the second stand part, that is assigned to a rotary joint connecting the second stand part to a first stand part is picked up. Then a control signal $M_c$ for setting the drive torque provided by means of the drive member is generated from the picked-up torque $M_I$ and a setpoint drive torque value $M_s$.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
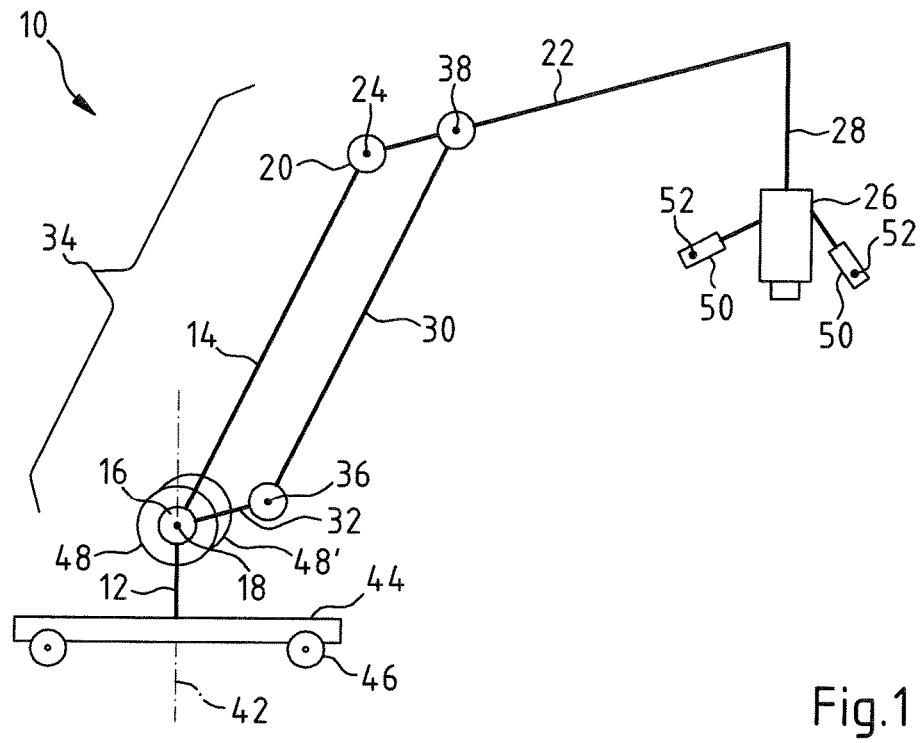
FIG. 1 shows a first stand for mounting a medical instrument in the form of a surgical microscope.

The stand 10 that is shown in FIG. 1 has a first stand part 12 in the form of a base, on which a second stand part 14, formed as a holding arm, is mounted in a pivotally movable manner in a rotary joint 16 with a horizontal axis of rotation 18. On the second stand part 14, formed as a holding arm, a supporting arm 22 is fastened in a pivotally movable manner in a rotary joint 20 and can be pivoted there about a horizontal axis of rotation 24. The supporting arm 22 supports a medical-optical instrument 26 on a front link 28. The supporting arm 22 of the stand 10 is jointedly connected to a vertical link 30, which is parallel to the second stand part 14 formed as a holding arm and on which there is articulated a further link 32, which is rotatably mounted on the first stand part 12 about the horizontal axis of rotation 18. The further link 32 can therefore be moved on the first stand part 12 about the horizontal axis of rotation 18 of the rotary joint 16 for the second stand part 14. The second stand part 14, the supporting arm 22, the link 30 parallel to the second stand part 14 and the further link 32 form a parallel linkage 34, which includes a rotary joint with the axis of rotation 36 and a rotary joint with the axis of rotation 38.

The first stand part 12 of the stand 10 is arranged in a rotary joint 40, which has a vertical axis of rotation 42, on a transporting unit 44, which has transporting rollers 46. On the transporting unit 44, the first stand part 12 with the parallel linkage 34 and the medical optical instrument 26 mounted on it can be moved, for example in an operating theatre in a hospital.

The stand 10 includes a first drive unit 48 with a drive module in the form of an electric motor, which is supported on the first stand part 12 and has an output coupled to the second stand part 14. In the stand 10 there is a further drive unit 48' with a drive module that is likewise supported on the first stand part 12. This drive module is also an electric motor and has an output coupled to the further link 32. The first drive unit 48 and the further drive unit 48' in each case includes a stand braking mechanism. The stand braking mechanism of the drive unit 48 serves the purpose of optionally enabling and disabling a rotational movement of the further stand part 14 relatively in relation to the first stand part 12 about the axis of rotation 18. With the stand braking mechanism of the drive unit 48' it is possible to optionally enable and disable a rotational movement of the further link 32 relatively in relation to the first stand part 12 about the axis of rotation 18.

The drive units 48, 48' of the stand 10 allow the force-free moving of the supporting arm 22 with the medical-optical instrument 26 mounted on it about the horizontal axis of rotation 24 and the horizontal axis of rotation 18. For controlling the stand braking mechanisms, in the drive units 48, 48' there are on the medical-optical instrument 26 two handles 50 with operating elements 52.

Figure 2:
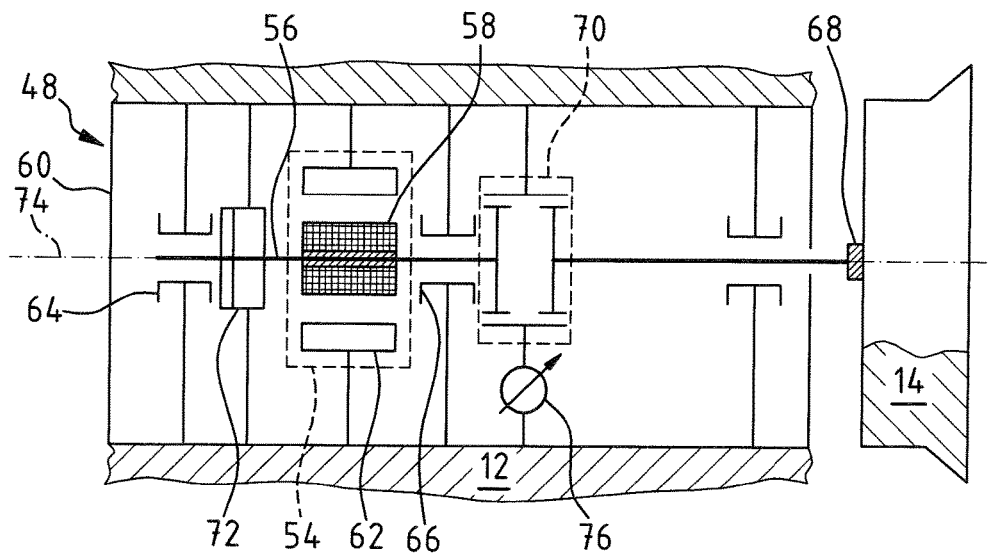
FIG. 2 shows a drive unit with a drive module in the stand.
Figure 3:
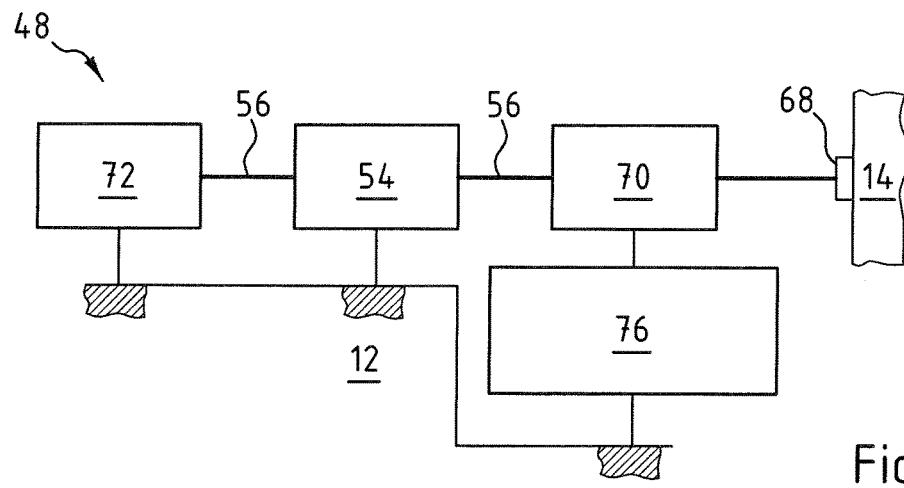
FIG. 3 shows an assembly diagram for the drive unit.

FIG. 2 shows the drive unit 48 as a section. FIG. 3 is an assembly diagram of the drive unit 48. The drive module 54, formed as an electric motor, has a rotor 58, which is connected for conjoint rotation to a drive member 56 formed as a drive shaft and includes a stator 62 fixed on the first stand part 12 by way of the housing 60 of the drive unit 48. The drive member 56 is rotatably mounted in the drive unit 48 in a first rotary bearing 64 and a further rotary bearing 66. The drive unit 48 has an output 68, which is connected for conjoint rotation to the second stand part 14 and is coupled to the drive member 56 by means of a step-down gear mechanism 70 formed as a harmonic-drive gear mechanism. The drive unit 48 includes a stand braking mechanism 72, which is supported on the housing 60 and with which a rotational movement of the drive member 56 about the axis of rotation 74 can be optionally enabled and disabled. In the drive unit 48 there is a torque sensor 76, which is integrated in the housing 60 of the drive unit 48 and is connected to the step-down gear mechanism 70 and the housing 60 of the drive unit 48 in order in this way to pick up in particular the torque in the form of a torque that is introduced into the second stand part 14 with respect to the axis of rotation 18 by the drive member 56 through the step-down gear mechanism 70 and the output 68. The further drive unit 48' has a construction corresponding to the configuration of the drive unit 48. With the torque sensor of the drive unit 48 it is possible to determine a torque that is introduced into the further link 32 with respect to the axis of rotation 18 and is present at the output of the step-down gear mechanism 70.

Figure 4:
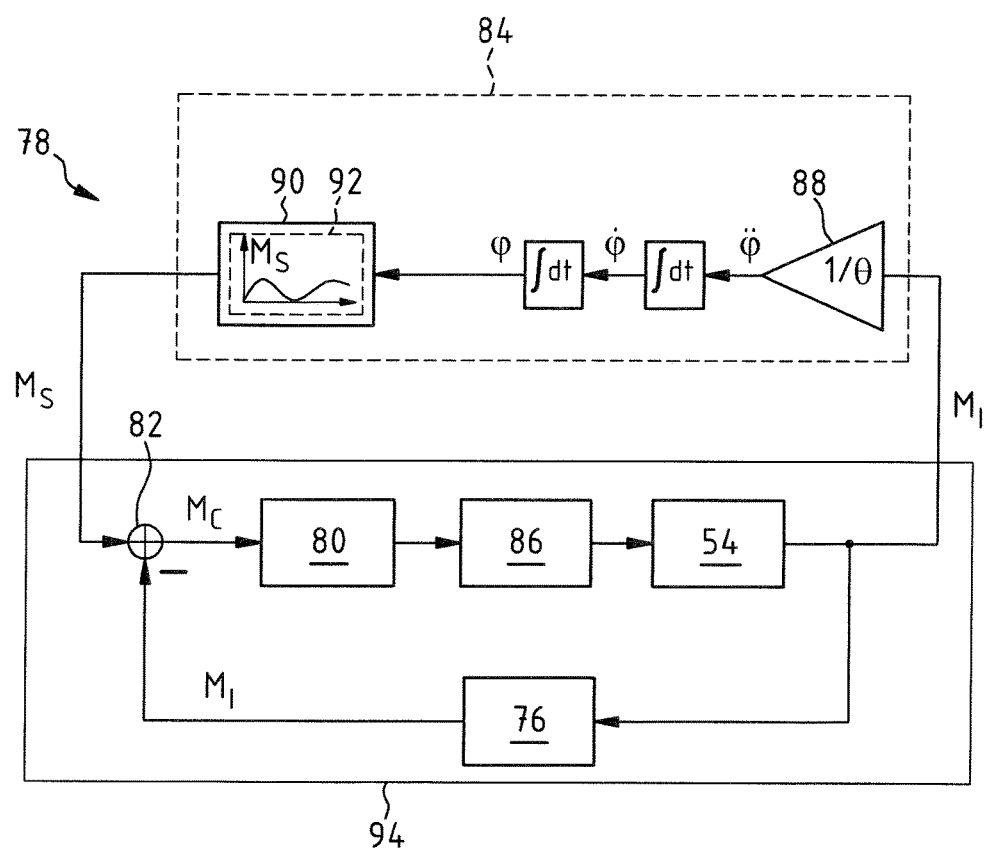
FIG. 4 shows a control device for the drive unit.

FIG. 4 shows the control device 78 for controlling the drive unit 48 in the stand 10. For controlling the drive unit 48' there is in the stand a further control device, which has a construction corresponding to the configuration of the control device 78.

The control device 78 includes a controller assembly 80, which is connected to the drive module 54 and is intended for setting the motor current on the basis of a control signal $M_c$ fed to the controller assembly 80 at an input. In the control device 78 there is a control-signal assembly 82 and an assembly for the determination of the setpoint drive torque value 84. For this, the control-signal signal assembly 82 forms the control signal $M_c$ from a sensor signal $M_I$, which is picked up by means of the torque sensor 76 and fed to the control-signal assembly 82 and a setpoint drive torque value $M_s$, which is fed to the control-signal assembly 82 from the assembly for the determination of the setpoint drive torque value 84. The control signal $M_c$ is a difference signal from the sensor signal $M_I$ and the setpoint drive torque value $M_s$. The controller assembly 80 is connected to a drive-module control 86, which includes power electronic assemblies for controlling the drive module 54. The control device 78 comprises an acceleration sensor 88, which determines as a movement signal the angular acceleration $\ddot{\varphi}$ of the second stand part 14 with respect to the axis of rotation 18. The assembly for the determination of the setpoint drive torque value 84 has a computer unit 90 and includes a data memory 92. In the assembly for the determination of the setpoint drive torque value 84, an angle setting of the second stand part 14 with respect to the first stand part 12 is determined from the signal of the acceleration sensor 88 by means of integration over a defined time interval. On the basis of a table stored in the data memory 92 with empirical data on setpoint drive torque values $M_s$ for a defined position of the second stand part 14 with respect to the first stand part 12 about the axis of rotation 18, a setpoint drive torque value $M_s$ is then determined on the basis of this table and the movement signal by a computer program in the computer unit 90 and is output to the control-signal assembly 82. The computer unit 90 can include a non-transitory storage medium and the computer program can be stored in the non-transitory storage medium.

In the control device 78, the control-signal assembly 82, the controller assembly 80, the drive-module control 86, the drive module 54 and the torque sensor 76 form a control loop 94, to which a setpoint drive torque value $M_s$ is fed from the assembly for the determination of the setpoint drive torque value 84 and which provides with the drive member 56 of the drive module 54 a drive torque $M_T$, which is introduced into the second stand part 14.

The control device 78 for controlling the drive unit 48 in the stand 10 and the corresponding control device for controlling the further drive unit allow that, when the stand braking mechanisms 72 are open, the medical-optical instrument 26 can be moved in a substantially force-free manner by adjusting the parallel linkage 34, because the drive units 48, 48' compensate for the load torques occurring in the axes of rotation of the stand 10. It should be noted that an angle sensor may also be provided for determining the angular position of the second stand part 14 with respect to the first stand part 12 in the stand 10, or a sensor for picking up the angular velocity of the movement of the second stand part 14 about the axis of rotation 18 on the first stand part 12.

Figure 5:
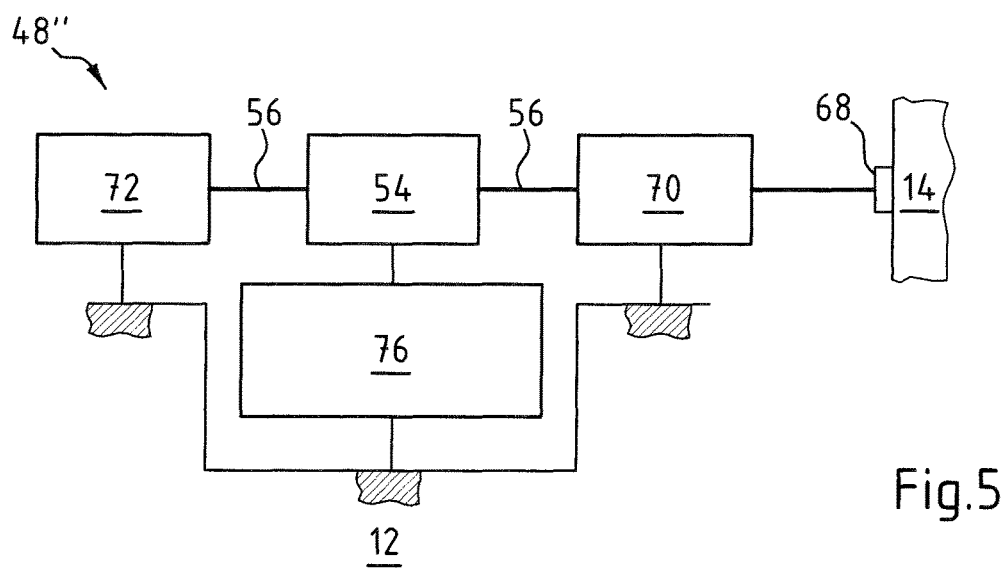
FIG. 5 shows an assembly diagram for an alternative drive unit.

FIG. 5 is an assembly diagram of a drive unit 48" functionally corresponding to the drive unit 48, with an alternative construction. Assemblies of the drive unit 48 and the drive unit 48" that correspond to one another have the same designations in FIG. 3 and in FIG. 5. The torque sensor 76 is connected to the first stand part 12 and the drive module 54, in order in this way to pick up the torque $M_I$ that is introduced into the second stand part 14 with respect to the axis of rotation 18 by the drive member 56 through the step-down gear mechanism 70 and the output 68 and further torques, acting on the second stand part 14.

Figure 6:
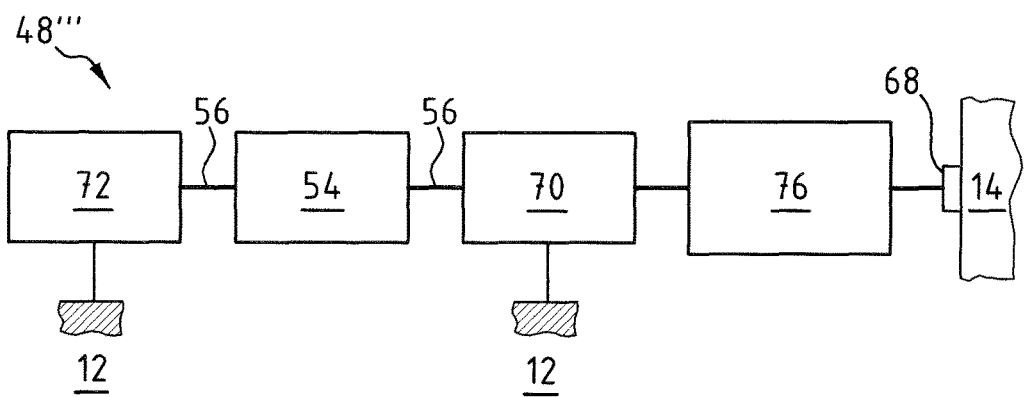
FIG. 6 shows an assembly diagram for a further, alternative drive unit.

FIG. 6 is an assembly diagram of a further drive unit 48''' functionally corresponding to the drive unit 48, with an alternative construction. Assemblies of the drive unit 48 and the drive unit 48''' that correspond to one another have the same designations in FIG. 3 and in FIG. 6. The torque sensor 76 is arranged ranged here between the step-down gear mechanism 70 and the output 68, in order to pick up a torque $M_I$ that is introduced into the second stand part 14 with respect to the axis of rotation 18.

Figure 7:
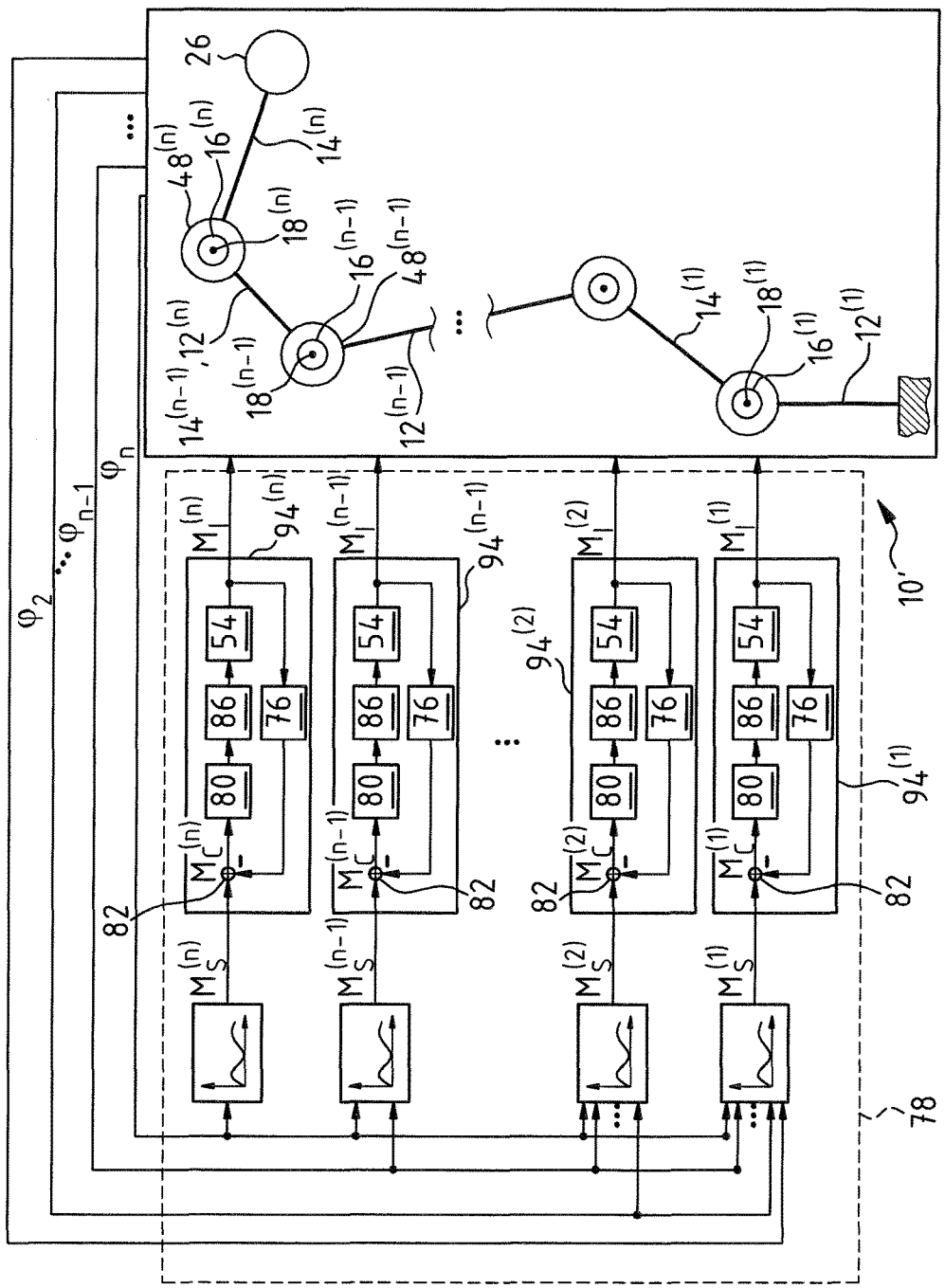
FIG. 7 shows a second stand for mounting a medical instrument.

FIG. 7 shows a second stand 10' with a medical-optical instrument 26 mounted on it and with multiple rotary joints $16^{(n)}, 16^{(n-1)}, \ldots, 16^{(1)}$ with axes of rotation $18^{(n)}, 18^{(n-1)}, \ldots, 18^{(1)}$, which respectively connect a first stand part $12^{(n)}, 12^{(n-1)}, \ldots, 12^{(1)}$ to a second stand part $14^{(n)}, 14^{(n-1)}, \ldots, 14^{(1)}$. Each of the rotary joints $16^{(n)}, 16^{(n-1)}, \ldots, 16^{(1)}$ is respectively assigned here a drive unit $48^{(n)}, 48^{(n-1)}, \ldots, 48^{(1)}$ and a control loop $94^{(n)}, 94^{(n-1)}, \ldots, 94^{(1)}$ with a torque sensor 76 for picking up the torque $M_I^{(n)}$ introduced into the second stand part $14^{(n)}$, $14^{(n-1)}), \ldots, 14^{(1)}$, in particular by way of the respective drive member 56, which has in each case a construction corresponding to the control loop 94 that is shown in FIG. 4. In the stand 10', each of the rotary joints $16^{(n)}, 16^{(n-1)}, \ldots, 16^{(1)}$ has a position sensor or encoder, which indicates the momentary angular position $\varphi^{(n)}, \varphi^{(n-1)}, \ldots, \varphi^{(1)}$ of the rotary joint $16^{(n)}, 16^{(n-1)}, \ldots, 16^{(1)}$. The stand 10' includes a control device 78 with an assembly for the determination of the setpoint drive torque value 84, which determines the setpoint drive torque value $M_s^{(n)}$ for each drive unit $48^{(n)}, 48^{(n-1)}, \ldots, 48^{(1)}$ on the basis of the position of the rotary joints $16^{(n)}, 16^{(n-1)}, \ldots, 16^{(1)}$ and their arrangement from one or more corresponding angular positions $\varphi^{(n)}, \varphi^{(n-1)}, \ldots, \varphi^{(1)}$ of the rotary joints $16^{(n)}, 16^{(n-1)}, \ldots, 16^{(1)}$.

Figure 8:
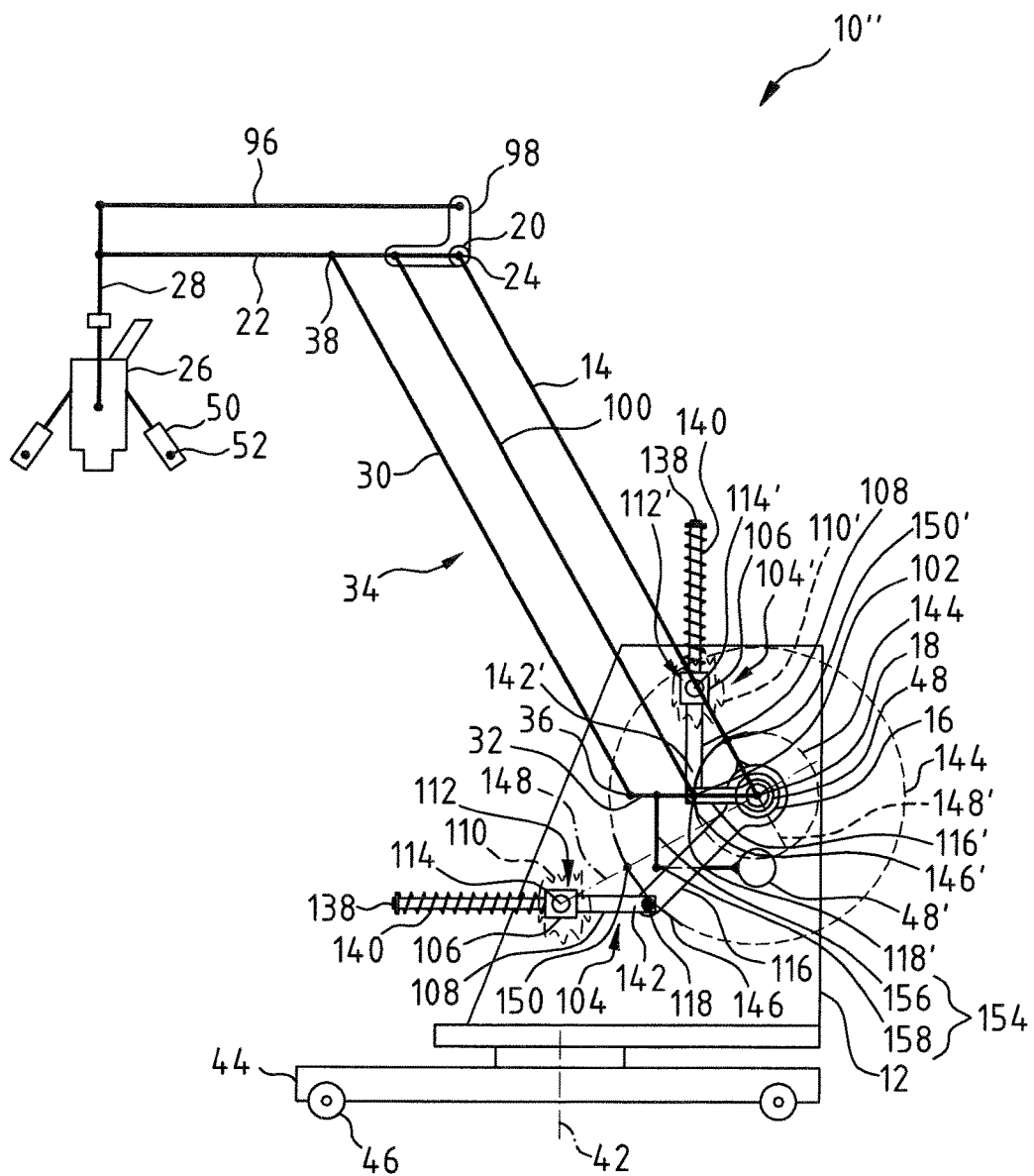
FIG. 8 shows a third stand for mounting a medical instrument in the form of a surgical microscope; and, FIG. 9 shows a fourth stand for mounting a medical instrument.

FIG. 8 shows a third stand 10" for mounting a medical instrument 26 formed as a surgical microscope. As far as the assemblies of the stand that is shown in FIG. 1 correspond to the assemblies of the stand 10", they are identified by the same numerals as reference signs. The stand 10" has a first stand part 12, which is formed as a base and connected to which as a second stand part 14 is a holding arm with a rotary joint 16. The second stand part 14, formed as a holding arm, can be moved in the rotary joint 16 about a horizontal axis of rotation 18. On the second stand part 14, formed as a holding arm, a supporting arm 22 is fastened in a pivotally movable manner in a rotary joint 20 and can be pivoted there about a horizontal axis of rotation 24. The supporting arm 22 supports the medical-optical instrument 26 on a front link 28. The front link 28 is connected by way of a compensating link 96 to a crank link 98, which is rotatably mounted on the second stand part 14 in a rotary joint with the axis of rotation 24. This crank link 98 is supported by means of a further link 100, which is jointedly connected to the crank link 98, on the first stand part 12 in a rotary joint 102. Torques that are introduced into the front link 28 are in this way transferred to the crank link 98 and introduced into the first stand part 12.

The supporting arm 22 of the stand 10" is jointedly connected to a vertical link 30, which is parallel to the second stand part 14, formed as a holding arm, and articulated on which is a further link 32, which is rotatably mounted on the first stand part 12 about the horizontal axis of rotation 18. The further link 32 can therefore be moved on the first stand part 12 about the horizontal axis of rotation 18 of the rotary joint 16 for the second stand part 14. The second stand part 14, the supporting arm 22, the link 30 parallel to the second stand part 14 and the further link 32 form a parallel linkage 34, which includes a further rotary joint with the axis of rotation 36 and a further rotary joint with the axis of rotation 38. To compensate at least partially for the load torque $D_L, D_{L'}$, that is caused by the load of the medical-optical instrument 26 and the mass of the parallel linkage 34 and also the links 28, 96, 98, 100 about the axis of rotation 18, in the stand 10" there are on the one hand a holding member 104 and a further holding member 104' with an elastically deformable energy store 140 and on the other hand a drive unit 48 and a further drive unit 48'.

The holding member 104 and the further holding member 104' have in each case a first holding member part 106 and a second holding member part 108, which is displaceable in a linearly movable manner in relation to the first holding member part 106. The first holding member part 106 of the holding member 104 and of the further holding member 104' is in each case mounted on a holding portion 110 of the first stand part 12 in a rotary bearing 112, 112' and can be moved there relatively in relation to the first stand part 12 about a horizontal axis of rotation 114, 114'. The second holding member part 108 is in this case connected to a connection portion 116, which is fixedly connected to a second stand part, and to a connection portion 116', which is fixedly connected to the further link 32, and respectively held there in a rotary bearing with an axis of rotation 118, 118'. The second holding member part 108 is formed in each case as a rod-like body. It has a section 136 facing the respective connection portion 116, 116' and a section 138 facing away from the respective connection portion 116, 116'. The holding member 104, 104' includes in each case an elastically deformable energy store 140. The elastically deformable energy store 140 is preferably a spring formed as a compression spring.

The second holding member part 108 of the holding member 104 has a connection point 142, which is for connecting to the connection portion 116 of the second stand part 14 and, when there is pivoting of the second stand part 14 about the first axis of rotation 18, describes a path of movement 146 lying on an imaginary circular line 144 around the axis of rotation 18. The imaginary circular line 144 has a point of intersection 150 with a straight line 148 passing perpendicularly through the first axis of rotation 18 and the further axis of rotation 114, the point of intersection lying between the first axis of rotation 118 and the further axis of rotation 114. The second holding member part 108 of the further holding member 104' has a connection point 142', which is for connecting to the connection portion 116' of the further link 32 and, when there is pivoting of the further link 32 about the first axis of rotation 18, describes a path of movement 146' lying on an imaginary circular line 144' around the axis of rotation 18. The imaginary circular line 144' has in this case a common point of intersection 150' with a straight line 148' passing perpendicularly through the first axis of rotation 18 and the further axis of rotation 114', the point of intersection lying between the first axis of rotation 118 and the further axis of rotation 114'.

The drive unit 48 in the stand 10" includes a drive module which is for moving the second stand part 14 about the axis of rotation 18 of the rotary joint 16, is supported on the first stand part 12 and is rotatably coupled to the second stand part 14. The drive unit 48' has a drive module, which is supported on the first stand part 12 and is rotatably coupled to the further link 32 by way of a coupling gear mechanism 154 with the links 156, 158 forming a link chain. The drive unit 48 and the drive unit 48' have in each case a construction described above on the basis of FIG. 2 and FIG. 3. For controlling the drive units 48, 48', the stand 10" includes in each case a control device, which has a construction described above on the basis of FIG. 4. The drive units 48, 48' allow that a load torque about the axis of rotation 36, 38 that is only partially compensated by means of the holding members 104, 104' with the elastically deformable energy store 140 can be completely compensated by means of motor force. Then, with the stand braking mechanisms open, the stand 10" can be moved by the operator using the handles 50 in a force-free manner, since the operator only has to overcome forces of inertia.

Figure 9:
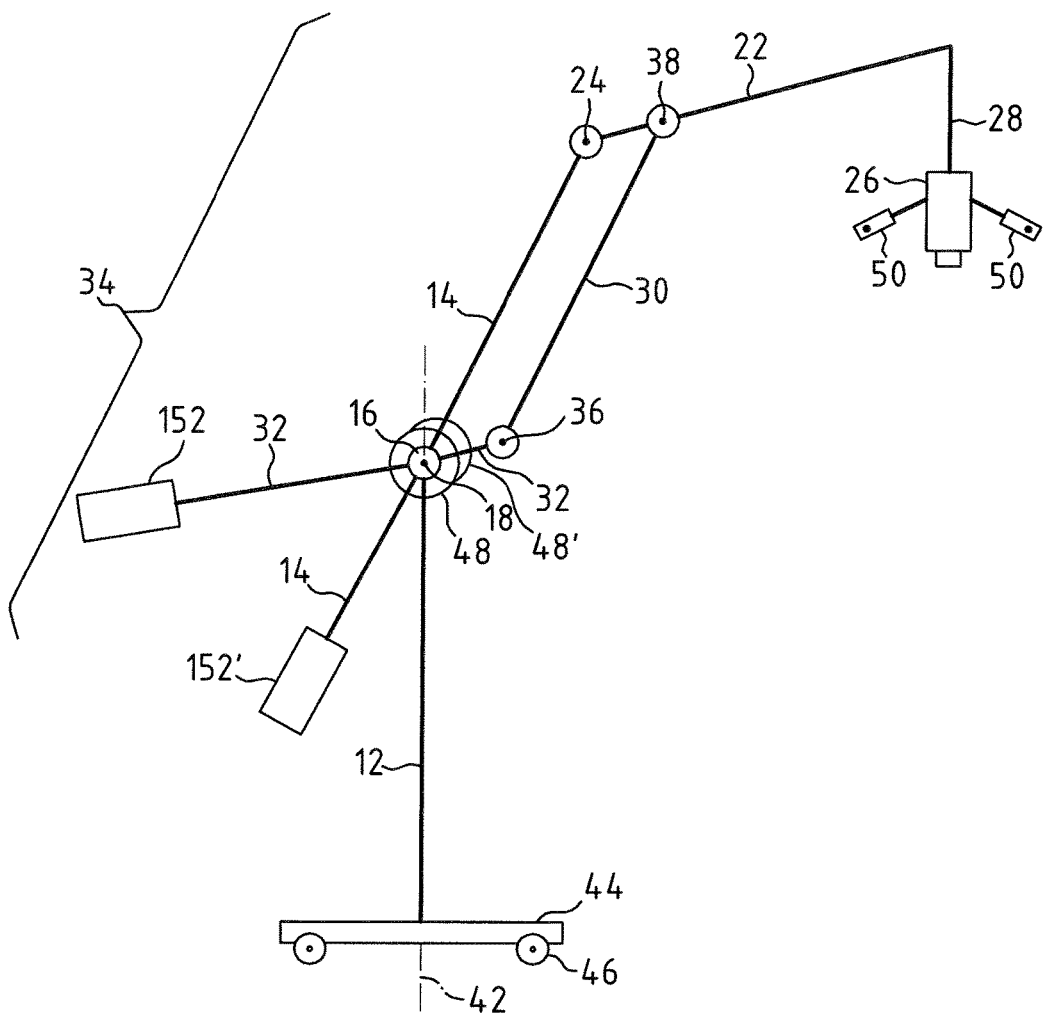

FIG. 9 shows a fourth stand 10''' for mounting a medical-optical instrument 26 formed as a surgical microscope. As far as the assemblies of the stand that is shown in FIG. 1 correspond to the assemblies of the stand 10''', they are identified by the same numerals as reference signs. In the stand 10''' there are compensating masses 152, 152', which partially compensate for a load torque caused by the medical-optical instrument 26 in the axes of rotation 18, 24. In this way it can be achieved that the drive modules in the drive units 48, 48' can be made comparatively small, since it is consequently then only necessary to compensate for correspondingly reduced residual load torques in the axes of rotation 18, 24, 38, 36 of the parallel linkage 34.

It should be noted that, as an alternative or in addition to the compensating masses in the stand, cable systems and/or chain systems with compensating masses and torsion springs may be provided, in order in this way to produce torques that counteract a load torque in the axes of rotation of the stand.

To sum up, the following preferred features of the invention should be noted in particular: A stand 10, in particular for mounting a medical-optical instrument 26, for example a surgical microscope, has a first stand part 12 and includes a second stand part 14, which is connected to the first stand part 12 in a rotationally movable manner by means of a rotary joint 16 and can be moved relatively in relation to the first stand part 12 about an axis of rotation 18. The stand 10 has a drive module 54, which is supported on the first stand part 12 and has a drive member 56 coupled to the second stand part 14. The stand 10 includes a control device 78 comprising a controller assembly 80, which is connected to the drive module 54 and is intended for setting a drive torque that is provided by the drive member 56 of the drive module 54. In the control device 78 there are a torque sensor 76 for picking up a torque $M_I$ introduced into the second stand part 14, that is, a torque $M_I$ that is acting on the second stand part 14, and a control-signal assembly 82, which is connected to the controller assembly 80 and generates from the torque $M_I$ picked up by means of the torque sensor 76 and a setpoint drive torque value $M_s$ transmitted to the control-signal assembly 82 a control signal $M_c$, which is fed to the controller assembly 80 and is intended for setting the drive torque provided by the drive member 56 of the drive module 54.

It is understood that the foregoing description is that of the preferred embodiments of the invention and that various changes and modifications may be made thereto without departing from the spirit and scope of the invention as defined in the appended claims.

LIST OF REFERENCE SIGNS

10, 10', 10", 10''' Stand
12 First stand part
$12^{(n)}, 12^{(n-1)}, \ldots, 12^{(1)}$ First stand part
14 Second stand part
$14^{(n)}, 14^{(n-1)}, \ldots, 14^{(1)}$ Second stand part
16, $16^{(n)}, 16^{(n-1)}, 16^{(1)}$ Rotary joint
18, $18^{(n)}, 18^{(n-1)}, \ldots, 18^{(1)}$ Axis of rotation
20 Rotary joint
22 Supporting arm
24 Horizontal axis of rotation
26 Medical-optical instrument
28 Front link
30; 32 Link
34 Parallel linkage
36, 38 Axis of rotation
40 Rotary joint
42 Axis of rotation
44 Transporting unit
46 Transporting roller
48, 48', 48", 48''' Drive unit
$48^{(n)}, 48^{(n-1)}, \ldots, 48^{(1)}$ Drive unit
50 Handle
52 Operating element
54 Drive module 56 Drive member
58 Rotor
60 Housing
62 Stator
64, 66 Rotary bearing
68 Output
70 Step-down gear mechanism
72 Stand braking mechanism
74 Axis of rotation
76 Torque sensor
78 Control device
80 Controller assembly
82 Control-signal assembly
84 Assembly for determination of the setpoint drive torque value
86 Drive-module control
88 Acceleration sensor
90 Computer unit
92 Data memory
94 Control loop
$94^{(n)}, 94^{(n-1)}, 94^{(1)}$ Control loop
96 Compensating link
98 Crank link
100 Further link
102 Rotary joint
104 Holding member
104' Further holding member
106, 108 Holding member part
110 Holding portion
112, 112' Rotary bearing
114, 114' Further horizontal axis of rotation
116, 116' Connection portion
118, 118' First axis of rotation
136 Facing section
138 Facing-away section
140 Energy store
142, 142' Connection point
144, 144' Circular line
146, 146' Path of movement
148, 148' Straight line
150, 150' Point of intersection
152, 152' Compensating mass / counterweight
154 Coupling gear mechanism
156, 158 Link

What is claimed is:

1. A stand comprising:
a first stand part;
a rotary joint defining an axis of rotation;
a second stand part connected to said first stand part in a rotationally movable manner via said rotary joint;
said second stand part being configured to be movable about said axis of rotation relative to said first stand part;
a drive module supported on said first stand part;
said drive module having a drive member coupled to said second stand part;
a control device having a controller assembly;
said controller assembly being connected to said drive module and being configured to set a drive torque applied by said drive member of said drive module to said second stand part in dependence upon a control signal (Mc);
said control device including a torque sensor configured to detect a torque (Mi) applied by said drive module to said second stand with respect to said axis of rotation;
said control device further including a control-signal assembly connected to said controller assembly and a sensor assembly operatively connected to said second stand part for providing a set point drive torque valve (Ms) in response to a movement of said second stand part about said axis of rotation;
said control-signal assembly being configured to generate said control signal (Mc) from said torque (Mi) detected by said torque sensor and said set point drive torque value (Ms) transmitted to said control-signal assembly from said sensor assembly;
said controller assembly being connected to said control-signal assembly to receive said control signal (Mc); and,
said control signal (Mc) being applied to said drive module via said controller assembly to adjust said drive torque transmitted to said second stand part by said drive member of said drive module.

2. The stand of claim 1, wherein the stand is configured to receive medical optical apparatus.

3. The method of claim 1, wherein the stand is configured to receive a surgical microscope.

4. The stand of claim 1, wherein said control signal (Mc) generated by said control-signal assembly is a difference signal formed from the torque (Mi) detected by said torque sensor and said setpoint drive torque value (Ms).

5. The stand of claim 1, wherein said sensor assembly includes:
an acceleration sensor configured to determine a movement signal for a rotational movement of said second stand part about said axis of rotation from at least one of an angle of rotation ($\varphi$), a change in the angle of rotation ($\dot{\varphi}$), and an acceleration of the angle of rotation ($\ddot{\varphi}$); and,
said control device including a setpoint determination unit configured to determine the setpoint drive torque value (Ms) from said movement signal.

6. The stand of claim 5, wherein said setpoint determination unit includes a computer unit having a computer program stored therein for calculating the setpoint drive torque value (Ms) from said movement signal.

7. The stand of claim 1, wherein said drive module is configured as an electric motor.

8. The stand of claim 1, further comprising:
a gear mechanism; and
said drive module having an output coupled to said second stand part via said gear mechanism.

9. The stand of claim 8, wherein said gear mechanism includes a step-down gear mechanism connected to said output.

10. The stand of claim 9, wherein said step-down gear mechanism is configured as a harmonic-drive gear mechanism.

11. The stand of claim 8, wherein said gear mechanism includes a gear assembly having a coupling gear mechanism connected to said second stand part.

12. The stand of claim 8, wherein:
said gear mechanism has an output connected to said second stand part; and,
said torque sensor is configured to determine the torque that is introduced into said output of said gear mechanism.

13. The stand of claim 1 further comprising at least one of a stand braking mechanism configured to optionally enable and disable a movement of said first stand part relative to said second stand part about the axis of rotation of said rotary joint, a counterweight, and an elastically deformable energy store configured to at least partially compensate for a load torque ($M_L$) about the axis of rotation that is introduced into said second stand part.

14. The stand of claim 1 further comprising:
a supporting arm configured for mounting a medical-optical instrument;
said first stand part being formed as a base on which the second stand part is mounted;
said second stand part being a holding arm;
said supporting arm being connected to said holding arm in a pivotally movable manner;
a first link connected in a rotationally movable manner to said supporting arm;
said axis of rotation being a first axis of rotation;
a second link connected to said first stand part and being displaceable in a pivotally movable manner about said first axis of rotation;
said first link, said supporting arm, said second link and said second stand part conjointly forming a parallel linkage;
a second drive module supported on said first stand part and having a second drive member that is coupled to said second link;
a second control device having a second controller assembly which is connected to said second drive module and is configured for setting a second drive torque provide by said second drive member of said second drive module;
said second control device including a second torque sensor configured to detect a second torque acting on said second link and a second control-signal assembly, which is connected to said second controller assembly;
said second control-signal assembly being configured to generate from said second torque detected via said second torque sensor and a second setpoint drive torque value (Ms) transmitted to said second control-signal assembly a second control signal (Mc) which is fed to said second controller assembly and is configured for setting a drive torque provided by the second drive member of said second drive module.

15. A stand comprising:
a plurality of first stand parts;
a plurality of second stand parts;
a plurality of rotary joints each connecting one of said first stand parts to a corresponding one of said second stand parts;
each of said second stand parts being configured to the movable about a corresponding axis of rotation relative to the corresponding one of said first stand parts;
a plurality of drive modules each being assigned to a respective one of said rotary joints and being supported on a corresponding one of said first stand parts;
said plurality of drive modules each having an output connected to a corresponding one of said second stand parts and a drive member coupled to a corresponding one of said second stand parts via the corresponding one of said outputs;
a control device including a plurality of control loops;
each of said control loops being configured for one of said drive modules and each having a torque sensor to detect a torque (Mi) acting on the corresponding one of said second stand parts;
said control device including a controller assembly;
said controller assembly being connected to said drive modules and being configured to set a drive torque applied by each of said outputs of said drive modules to corresponding ones of said second stand parts in dependence upon a corresponding control signal (Mc);
said control device further including a control-signal assembly connected to said controller assembly for each of said control loops and sensor assembly for each of said control loops operatively connected to a corresponding one of said second stand parts for providing a set point drive torque signal (Ms) in response to a movement of said corresponding stand part;
said controller assembly being connected to said controller assembly to receive said control signal (Mc); and,
said control signal (Mc) being to said drive module via said controller assembly to adjust said drive torque transmitted to the corresponding second stand part by the drive member and output connected to the corresponding second stand part.

16. The stand of claim 15 further comprising:
plurality of acceleration sensors each configured to determine a movement signal for a rotational movement of one of said second stand parts about the corresponding one of said axes of rotation from at least one of an angle of rotation ($\varphi$), a change in the angle of rotation ($\varphi$), and an acceleration of the angle of rotation ($\varphi$); and,
said control device includes for each drive module assigned to a rotary joint a setpoint determination unit configured to determine the setpoint drive torque value (Ms) from said movement signal.

17. The stand of claim 16, wherein at least one of said setpoint determination units also takes into account for determining the setpoint drive torque value (Ms) at least one further movement signal for a rotational movement of another one of said second stand parts about the corresponding one of said axes of rotation.

18. A method for moving a medical-optical instrument mounted on a stand having a first stand part, a rotary joint defining an axis of rotation, a second stand part connected to the first stand part in a rotationally movable manner via the rotary joint, the second stand part being configured to be movable about said axis of rotation relative to the first stand part, a drive module supported on the first stand part, the drive module having a drive member coupled to the second stand part, a control device having a controller assembly, the controller assembly being connected to the drive module and being configured to set a drive torque applied by the drive member of the drive module to said second stand part in dependence upon a control signal (Mc), the control device including a torque sensor configured to detect a torque (Mi) applied by said drive module to the second stand part with respect to said axis of rotation, the control device further including a control-signal assembly connected to the controller assembly and a sensor assembly operatively connected to said second stand part for providing a set point drive torque value (Ms) in response to a movement of said second stand part about said axis of rotation; the control-signal assembly being configured to generate the control signal (Mc) from the torque detect (Mi) detected by the torque sensor and the setpoint drive torque value (Ms) transmitted to the control-signal assembly from said sensor assembly, the controller assembly being connected to the control-signal assembly to receive the control signal (Mc), and, the control signal (Mc) being applied to the drive module via the controller assembly to adjust the drive torque transmitted to the second stand part by the drive member of the drive module, the method comprising the steps of:
detecting the torque (Mi) acting on the second stand part; and,
generating the control signal (Mc) for setting the drive torque provided via the drive member from the detected torque (Mi) and the setpoint drive torque value (Ms).

19. The method of claim 18, wherein the method is for moving a surgical microscope mounted on a stand.

* * * * *

UNITED STATES PATENT AND TRADEMARK OFFICE
CERTIFICATE OF CORRECTION

PATENT NO. : 10,386,010 B2
APPLICATION NO. : 15/404111
DATED : August 20, 2019
INVENTOR(S) : C. Voigt et al.

Page 1 of 1

It is certified that error appears in the above-identified patent and that said Letters Patent is hereby corrected as shown below:

In the Specification

In Column 4:
Line 42: delete "age" after -- linkage --.

In Column 7:
Line 54: delete "ranged" after -- arranged --.

In the Claims

In Column 13:
Line 25: delete "provide" and substitute -- provided -- therefor.
Line 46: delete "configured to the" and substitute -- configured to be -- therefor.

In Column 14:
Line 16: add "a" before -- plurality --.
Line 20: delete "a change in the angle of rotation ($\varphi$)" and substitute -- a change in the angle of rotation $(\dot{\varphi})$ -- therefor.
Line 21: delete "the angle of rotation ($\varphi$);" and substitute -- the angle of rotation $(\ddot{\varphi})$; -- therefor.
Line 54: delete "detect" after -- the torque --.

Signed and Sealed this
Seventeenth Day of December, 2019

Andrei Iancu
*Director of the United States Patent and Trademark Office*